(12) United States Patent
Catania et al.

(10) Patent No.: US 8,513,381 B2
(45) Date of Patent: Aug. 20, 2013

(54) MELANOCORTIN ANALOGS WITH ANTIMICROBIAL ACTIVITY

(75) Inventors: Anna Catania, Milan (IT); Ferruccio Bonino, Milan (IT); Paolo Grieco, Milan (IT); Ettore Novellino, Milan (IT)

(73) Assignee: Fondazione IRCCS Ca' Granda-Ospedale Maggiore Policlinico, Milan (IT)

( * ) Notice: Subject to any disclaimer, the term of this patent is extended or adjusted under 35 U.S.C. 154(b) by 0 days.

(21) Appl. No.: 13/144,858

(22) PCT Filed: Jan. 19, 2009

(86) PCT No.: PCT/EP2009/000290
§ 371 (c)(1),
(2), (4) Date: Sep. 21, 2011

(87) PCT Pub. No.: WO2010/081492
PCT Pub. Date: Jul. 22, 2010

(65) Prior Publication Data
US 2012/0015873 A1    Jan. 19, 2012

(51) Int. Cl.
*A61K 38/08*     (2006.01)
*C07K 7/06*      (2006.01)
*A61P 31/04*     (2006.01)

(52) U.S. Cl.
USPC .......................................... 530/328; 514/2.4

(58) Field of Classification Search
None
See application file for complete search history.

(56) References Cited

U.S. PATENT DOCUMENTS

2003/0109453 A1    6/2003   Catania et al.
2005/0130901 A1    6/2005   Lipton et al.

OTHER PUBLICATIONS

Definition of analogue, from http://cancerweb.ncl.ac.uk/cgi-bin/omd?analogue, pp. 1-5, Accessed Jul. 7, 2005.*
A. Luigia et al., "Novel Peptides Alpha-MSH Analogs with High Candidacidal Activity" Journal of Peptide Science, vol. 14, No. 8, Suppl. S, p. 92, Aug. 2008 & 30th European Peptide Symposium, Helsinki, Finland, Aug. 31-Sep. 5, 2008.
G. Paolo et al., "Novel Alpha-Melanocyte Stimulating Hormone Peptide Analogues with High Candidacidal Activity." Journal of Medicinal Chemistry, vol. 46, No. 5, pp. 850-855, Feb. 27, 2003.
G. Paolo et al., "Design and Synthesis of Melanocortin Peptides with Candidacidal and Anti-TNF-Alpha Properties." Journal of Medicinal Chemistry, American Chemical Society, Washington, vol. 48, No. 5, pp. 1384-1388, Mar. 10, 2005.
C.K. Jayawickreme, "Discovery and Structure-Function Analysis of Alpha-MSH Antagonists." Journal of Biological Chemisty, American Society of Biolochemical Biologists, Birmingham, vol. 269, No. 47, pp. 29846-29854, Nov. 25, 1994.
U.G. Sahm et al., "Synthesis of 153N-6 Analogues and Structure-function Analysis at Murine Melanocortin-1 (MC1) Receptors." Peptides, vol. 20, No. 3, pp. 387-394, 1999.
Lee Sung-Ah et al., "Solution Structure and Cell Selectivity of Piscidin 1 and Its Analogues." Biochemistry, vol. 46, No. 12, pp. 3653-3663, Mar. 27, 2007.
L. Auriemma et al., "Novel Peptides Alpha-MSH Analogs with High Candidacidal Activity" Journal of Peptide Science, vol. 14, No. 8, Suppl. S, p. 92, Aug. 2008 & 30th European Peptide Symposium, Helsinki, Finland, Aug. 31-Sep. 5, 2008.
P. Grieco et al., "Novel Alpha-Melanocyte Stimulating Hormone Peptide Analogues with High Candidacidal Activity." Journal of Medicinal Chemistry, vol. 46, No. 5, pp. 850-855, Feb. 27, 2003.
P. Grieco et al., "Design and Synthesis of Melanocortin Peptides with Candidacidal and Anti-TNF-Alpha Properties." Journal of Medicinal Chemistry, American Chemical Society, Washington, US, vol. 48, No. 5, pp. 1384-1388, Mar. 10, 2005.
E. A. Jayawickreme, "Discovery and Structure-Function Analysis of Alpha-MSH Antagonists." Journal of Biological Chemistry, American Society of Biolochemical Biologists, Birmingham, US, vol. 269, No. 47, pp. 29846-29854, Nov. 25, 1994.
U.G. Sahm et al., "Synthesis of 153N-6 Analogues and Structure-Function Analysis at Murine Melanocortin-1 (MC1) Receptors." Peptides (New York), vol. 20, No. 3, pp. 387-394, 1999.
S-A. Lee et al., "Solution Structure and Cell Selectivity of Piscidin 1 and Its Analogues." Biochemistry, vol. 46, No. 12, pp. 3653-3663, Mar. 27, 2007.

* cited by examiner

*Primary Examiner* — Julie Ha
*Assistant Examiner* — Li Ni Komatsu
(74) *Attorney, Agent, or Firm* — Dickstein Shapiro LLP

(57) ABSTRACT

The present invention finds application in the therapeutic fields. In particular, it concerns new synthetic melanocortin peptides having improved antimicrobial activity.

12 Claims, 1 Drawing Sheet

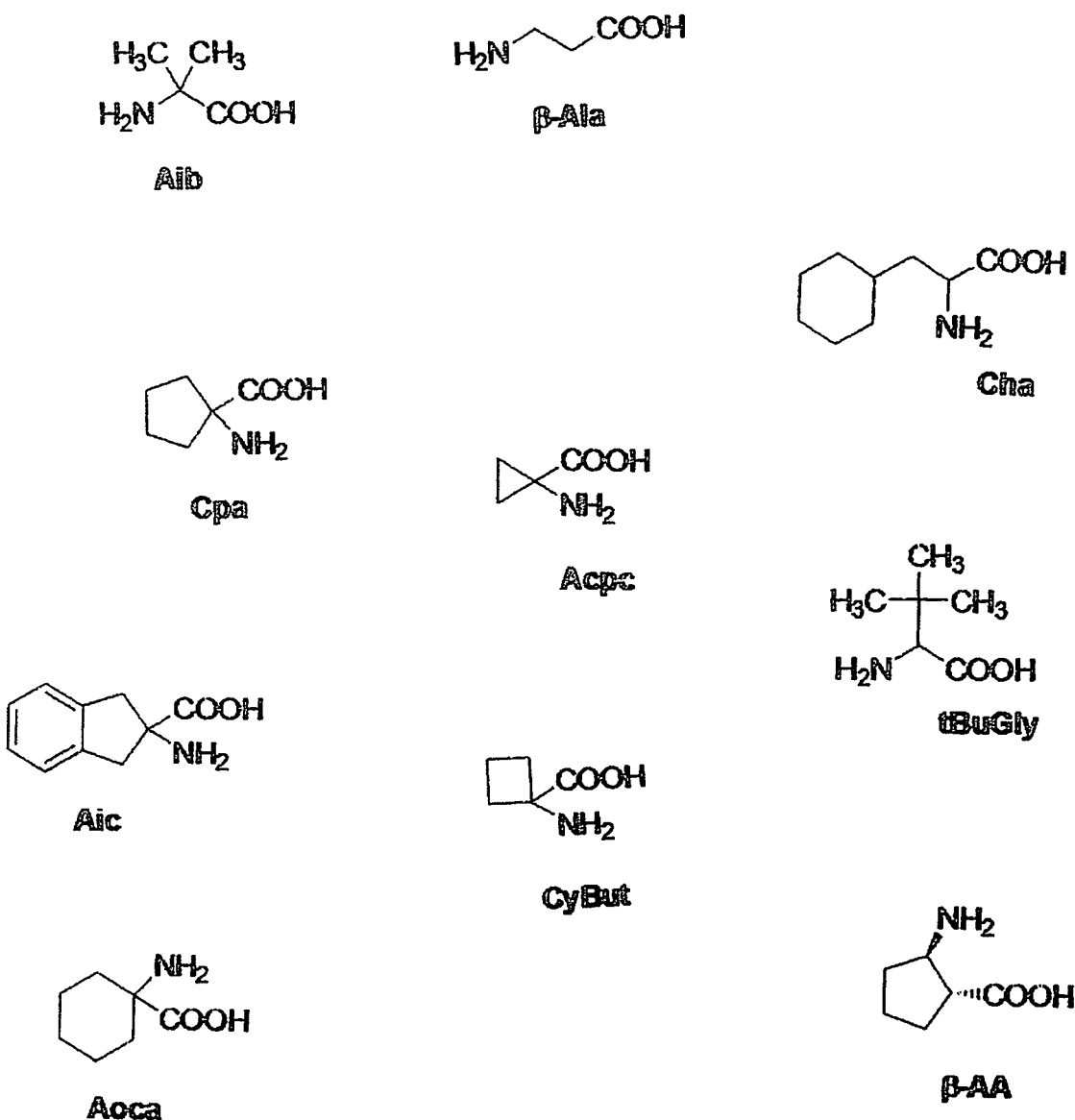

US 8,513,381 B2

MELANOCORTIN ANALOGS WITH ANTIMICROBIAL ACTIVITY

FIELD OF THE INVENTION

The present invention finds application in the therapeutic fields. In particular, it concerns new synthetic melanocortin peptides having improved antimicrobial activity.

BACKGROUND

Adrenocorticotropic hormone (ACTH) and α,β and γ-melanocyte stimulating hormone (α,β and γ-MSH) are generally referred to as melanocortin peptides or melanocortins for their common origin as posttranslational derivatives of pro-opiomelanocortin (POMC).

α-MSH is a tridecapeptide that exerts pleiotropic effects in several physiological pathways including modulation of fever and inflammation, control of feeding behaviour and energy homeostasis, control of autonomic functions and increase in melanogenesis. Researches explored the idea that α-MSH might exert beyond the established anti-inflammatory activity also anti-infective activity. Thus, α-MSH was found to have a potent antimicrobial activity, especially against *Candida albicans* and *Staphylococcus aureus*. *Candida albicans*, in particular, belongs to a group of fungi which may cause severe infections, i.e. candidosis, also comprising, for instance, *C. albicans, C. glabrata, C. krusei, C. Lusitaniae, C. stellatoidea, C. tropicalis, C. parapsilosis, C. pseudotropicalis, C. guilliermondii*. Under physiological conditions, said ubiquitous saprophytes are natural and inoffensive hosts of the health organism mucosa. However, when the natural defences, mainly represented by immunologic system, are weakened because of stress, pharmaceutical therapies, like with antibiotics, cortisone, immunosuppressant, cytostatic agents, contraceptives, or even radiotherapy, surgery interventions requiring insertion of a catheter or long lasting infusions or dialysis, inserted prosthesis, illnesses such as diabete, obesity or malnutrition, hyperthyroidism, tumors, or other events like burnings or trauma, especially in the infant or in elder patients, *Candida* may become a dangerous infective agent. In particular, infections may involve the skin, the respiratory tract, including mouth, throat and pharynx, the digestive apparatus or it may even cause infections to the urogenital apparatus or systemic infections to the cardio circulatory system, possibly causing endocarditis.

The analysis of the Melanocyte Stimulating Hormone peptide demonstrated that the sequence (6-13) contains the the invariant core sequence His-Phe-Arg-Trp (6-9) (SEQ ID NO 17), which is common to all melanocortin peptides and is responsible for the binding to the melanocortin receptors. Its C-terminal tripeptide Lys-Pro-Val (11-13) has been identified as relevant both for receptor activation and for the antimicrobial activity through the increase in cAMP. On the contrary, the N-terminal was not identified as having an influence on candidacidal activity. Further studies, such as, for instance, the alanine scan, indicate that the proline residue in position 12 has an important role for such activity.

In addition, Lys-11 and Pro-12 proved to be essential for the antimicrobial activity, in fact, their substitution causes the activity to be nearly abolished.

On the other hand, substitution in position 7 of the core sequence may enhance the potency of melanocortins. A substitution in position 7, such as, for instance, the replacement with D-Nal, increases the affinity of α-MSH for the melanocortin receptor MC4R. Substitution at position 12 with a more lipophilic amino acid, like Phe, resulted in a marked increase in candidacidal activity.

In spite of all the peptides already tested, there is still an unsatisfied need in the prior-art for more active compounds, which would cause less side effects to patients, thus resulting more tolerable, and which would also be safer and easier to be administered to patients as well as more stable, thus allowing the industrial preparation.

SUMMARY OF THE INVENTION

The present invention concerns new peptidic compound which have surprising activity against *Candida*. Said unexpected effects are linked to modifications of the structure of already known compounds with the introduction of non-natural amino-acids.

OBJECT OF THE INVENTION

Accordingly, it is a first object of the invention to provide synthetic melanocortin peptides having the amino acidic sequence corresponding to general formula (1) and to general subformula (1a).

In a further embodiment, the preferred peptides are those of dependent claims 2 to 8 and, in a preferred embodiment, the peptides are those of claim 9 and, in an even more preferred embodiment, the peptides are those of claim 10.

In a still further embodiment, the peptides of the invention are also those of general formula (1b) and, as a preferred embodiments, they are the peptides of claims 11 and 12.

As a second object, the present invention relates to said synthetic melanocortin peptides as a medicament, according to claim 13.

In a third object, the melanocortin peptides of the invention are antimicrobial medicaments as per claim 14.

In a preferred embodiment, the melanocortin peptides of the invention have candidacidal activity, as per claims 15 and 16 or they have antimicrobial activity against *S. aureus* or *P. aeruginosa* as per claim 17.

As a further preferred embodiment, the present invention relates to a pharmaceutical preparation, according to claims 18 to 23.

DESCRIPTION OF THE FIGURES

FIG. 1 shows non-conventional amino acids according to the present invention

DETAILED DESCRIPTION OF THE INVENTION

In a first embodiment, the present invention concerns melanocortin peptides having the amino acidic sequence of general formula (1):

$$W\text{-}A1\text{-}A2\text{-}A3\text{-}A4\text{-}X\text{-}A5\text{-}A6\text{-}A7\text{-}Y \tag{1}$$

wherein:

X is a non-conventional amino acid or X is one or more natural aromatic amino acids, preferably Phe, or the Gly-Gly dimer

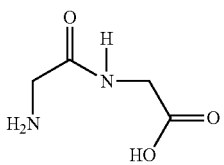

or the Ala-Ala dimer

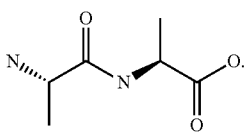

Alternatively, X may be Gly o a single bond.

In a preferred embodiment of the invention, X is a non-conventional amino acid.

Within the present invention, "non-conventional amino acids" includes any non natural occurring amino acids, i.e. those not genically encoded by a nucleotidic triplet, with respect to "natural amino acids", which are naturally occurring and encoded by a genomic triplet. "D" and "L" denote the amino acid configuration.

"Aromatic amino acid" is used with reference to natural aromatic amino acids, such as phenylalanine, tryptophan and tyrosine.

In a preferred embodiment, X is selected among Aib, β-Ala, Cha, Cpa, Acpc, tBuGly, Aic, Cybu, β-AA, Sar, (3,4-Cl)Ph, Tic or Aoca.

In a further preferred embodiment, X is Cha or Aic. The meanings of the above natural and non natural amino acid abbreviations are reported in Table 1 below and the rest of the description will adhere thereto.

TABLE 1

| | |
|---|---|
| Nal(1) or (1)Nal | 3-(1-Naphtyl)alanine |
| Nal(2) or (2)Nal | 3-(2-Naphtyl)alanine |
| Orn | Ornitine |
| Cit | Citrulline |
| Dap | 2,3-amino-propionic acid |
| Dab | 2,4-diammino-butiryc acid |
| Dpm | 2,2'-Diaminopimelic acid |
| Cha | Cyclohexyl-alanine |
| Aib | 2-aminoisobutiryc acid or α-methylalanine |
| β-Ala | beta-alanine; |
| Abu | 2-Aminobutyric acid |
| Cpa | 1-amino-cyclopentane carboxylic acid; |
| Acpc | 1-amino-cyclopropane carboxylic acid; |
| tBuGly | α-t-butylglycine or tert-leucine |
| Aic | 2-aminoindane-2-carboxylic acid; |
| Cybu | 1-amino-cyclobutane carboxylic acid |
| Aoca | 1-amino-cyclohexane carboxylic acid |
| β-AA | 2-aminocyclopentane carboxylic acid |
| Sar | Sarcosine |
| (3,4-Cl)Phe | 3,4-dichlore-L-Phenylalanine |
| Tic | Tetrahydroisoquinolinic-3-carboxylic acid |
| Ac | acetyl group |
| Nle | norleucine |
| (α-Me)Trp | α-methyltryptophan |
| Trp(CHO) | formyl-tryptophan |
| Trp(Me) | methyltryptophan |
| tert-Leu | tert-Butylglycin |

Other amino acids are disclosed using the conventional three-letter code.

In formula (1) above, W may be H or any suitable carboxy protecting groups, such as, for instance, a $C_1$-$C_8$ alkyl or alkanoyl; or W may be any D- or L-amino acids, such as, for instance, Ala, Nle, Gly, or the Gly-Gly dimer or the Ala-Ala dimer.

Alternatively, W may be the H-Glu-Thr-Pro-Asp tetrapeptide, thus giving the entire C-terminal of the native peptide.

The deletion of from 1 up to 4 amino acids starting from the native peptide C-terminal does not affect the activity of the peptide; accordingly, W may also be:

H-Thr-Pro-Asp

H-Pro-Asp; or even

H-Asp.

Alternatively, W may also be the H-Phe-Phe-His tripeptide.

Any of the above mentioned amino acidic residue may be either in D- or L-form.

A preferred protecting group for the carboxy-terminal may be, for example, an acyl group, such as, for instance, a C1-C8 straight or branched, satured or insatured carbo chain. The skilled person in the art will be able to select the most suitable carboxy-protecting groups or other carboxy-protecting groups may also be used as well known in the field of the invention.

A1 residue may be either the D- or the L-isomer of histidine or of any histidine analogues, such as, for instance, methyl-histidine or 6-carboxy-1,2,3,4-tetrahydro-imidazopyridin or any other histidine metabolic precursors or a charged amino acids, such as ornitine or lysine. Alternatively, A1 may be any natural amino acids. In a preferred embodiment, A1 is His.

A2 residue is D(2)Nal or it may be Phe, D-Phe, Nal(1), D-Nal(1), Nal(2), Tyr, D-Tyr or any other aromatic amino acids, both D- and L-isomer. Alternatively, A2 may be Isoleucine. In a preferred embodiment, A2 is D(2)Nal.

A3 residue may be Arg, Lys, Orn, Pro, Phe, (p-amino)Phe, or it may be Dap, Dab or Dpm.

In a preferred embodiment, A3 is Arginine.

A4 residue may be Trp or, alternatively, it may be (α-Me)Trp, Trp(Me), Trp(CHO) or Arg, all of them either in D- or in L-configuration, or A4 may be D-Nal(1) or D-Nal(2). In a preferred embodiment A4 is L-(α-Me)Trp, L-Trp(Me), L Trp (CHO) or, as the most preferred embodiment, L-Trp.

A5 residue may be either D- or L-isomer of Lys, Orn or it may be Dap or Dab. In a preferred embodiment, A5 is Lysine.

A6 residue may be either D- or L-isomer of Phe, Pro, Nal(1), Nal(2) or may be any other aromatic amino acids. In a preferred embodiment, A6 is Phe.

A7 residue may be either D- or L-isomer and may be Val, Thr, Leu, Ile, tert-Leu, Nle or it may be Abu. In a preferred embodiment, A7 is Val.

Y is the N-terminal of the peptide of general formula (1) and may be any suitable protecting groups, such as, for instance, an hydroxyl group (—OH), thus leading to an oxime terminal (—NHOH) or an acyl group, thus leading to an amidic terminal.

In a preferred embodiment, the peptides of the invention are those of general formula (1a) below:

W-His-D(2)Nal-Arg-Trp-X-Lys-Phe-Val-Y    (1a)

wherein X, W and Y have any of the above mentioned meanings. In an even preferred embodiment, the peptides of the invention are those listed in the following Table 2:

TABLE 2

| PEPTIDE | SEQUENCE | SEQ ID NO (CORE SEQUENCE) |
| --- | --- | --- |
| MSH0701 | H-His-D(2)-Nal-Arg-Trp-Gly-Gly-Lys-Phe-Val-NH2 | 1 (His-Ala-Arg-Trp-Gly-Gly-Lys-Phe-Val) |
| MSH0702 | H-His-D(2)-Nal-Arg-Trp-Aib-Lys-Phe-Val-NH2 | 2 (His-Ala-Arg-Trp-Aib-Lys-Phe-Val) |
| MSH0703 | H-His-D(2)-Nal-Arg-Trp-Ala-Lys-Phe-Val-NH2 | 3 (His-Ala-Arg-Trp-β-Ala-Lys-Phe-Val) |
| MSH0704 | H-His-D(2)-Nal-Arg-Trp-Cha-Lys-Phe-Val-NH2 | 4 (His-Ala-Arg-Trp-Cha-Lys-Phe-Val) |
| MSH0705 | H-His-D(2)-Nal-Arg-Trp-Cpa-Lys-Phe-Val-NH2 | 5 (His-Ala-Arg-Trp-Cpa-Lys-Phe-Val) |
| MSH0706 | H-His-D(2)-Nal-Arg-Trp-Acpc-Lys-Phe-Val-NH2 | 6 (His-Ala-Arg-Trp-Acpc-Lys-Phe-Val) |
| MSH0707 | H-His-D(2)-Nal-Arg-Trp-tBuGly-Lys-Phe-Val-NH2 | 7 (His-Ala-Arg-Trp-tBuGly-Lys-Phe-Val) |
| MSH0708 | H-His-D(2)-Nal-Arg-Trp-Aic-Lys-Phe-Val-NH2 | 8 (His-Ala-Arg-Trp-Aic-Lys-Phe-Val) |
| MSH0709 | H-His-D(2)-Nal-Arg-Trp-Cybu-Lys-Phe-Val-NH2 | 9 (His-Ala-Arg-Trp-Cybu-Lys-Phe-Val) |
| MSH07010 | H-His-D(2)-Nal-Arg-Trp-β-AA-Lys-Phe-Val-NH2 | 10 (His-Ala-Arg-Trp-β-AA-Lys-Phe-Val) |
| MSH07012 | H-His-D(2)-Nal-Arg-Trp-Aoca-Lys-Phe-Val-NH2 | 11 (His-Ala-Arg-Trp-Aoca-Lys-Phe-Val) |
| MSH07013 | H-His-D(2)-Nal-Arg-Trp-Phe-Lys-Phe-Val-NH2 | 12 (His-Ala-Arg-Trp-Phe-Lys-Phe-Val) |

In particular, MSH0704 and MSH0708 are the preferred peptides.

In a further preferred embodiment, the present invention concerns the peptides having general formula (1b) as follows:

$$W-A1-A2-A3-A4-2'-A5-A6-A7-Y \qquad (1b)$$

wherein
W is H-Phe-Phe-His;
Y is a amino terminal group as above disclosed;
A1 is His;
A2 may be Ile, Phe, (D)2-Nal;
A3 may be Arg or Phe;
A4 may be Arg, Trp, or Gly;
A5 is Lys;
X may be Gly or a single bond;
A6 may be Pro or Phe; and
A7 may be Val.

In particular, the compounds within formula (1) having general formula (1b) may have one of the following formula:

H-Phe-Phe-His-His-Ile-Phe-Arg-Gly-Lys-Pro-Val-NH2   (SEQ ID NO 13;
                                                    Phe-Phe-His-His-Ile-Phe-Arg-Gly-Lys-Pro-Val)

H-Phe-Phe-His-His-Phe-Arg-Trp-Gly-Lys-Phe-Val-NH2   (SEQ ID NO 14;
                                                    Phe-Phe-His-His-Phe-Arg-Trp-Gly-Lys-Phe-Val)

H-Phe-Phe-His-His-(D)2-Nal-Arg-Trp-Gly-Lys-Phe-Val-NH2 (SEQ ID NO 15;
                                                    Phe-Phe-His-His-Ala-Arg-Trp-Gly-Lys-Phe-Val)

H-Phe-Phe-His-His-Phe-Arg-Gly-Lys-Pro-Val-NH2       (SEQ ID NO 16;
                                                    Phe-Phe-His-His-Phe-Arg-Gly-Lys-Pro-Val)

According to the second embodiment, the peptides of the invention may be used as a medicament.

In particular, as per the third object of the invention, the disclosed peptides unexpectedly show antimicrobial activity and, more in particular, candidacidal activity, which is superior to the peptides known from the prior-art.

In fact, the compounds of the present invention have been surprisingly found to be very active against *Candida*, thus, they may usefully used for the treatment of pathologies cause by *Candida* fungi.

The compounds of the present invention have been found to be particularly active against *C. albicans, C. glabrata* and *C. krusei*.

In particular, against *C. albicans* strains ATCC 76615, ATCC 24433 or strains 995439, 995147, 000954, 991185, 994199, 983201-R1, 011587; against *C. glabrata* strains 18012, 995667, 995651 and against *C. krusei* strains 995668, 991388, 004490.

In particular, the results are shown in Example 2, which shows that compounds MSH0704 and MSH0708 are the most active ones.

In particular, they have the lowest MIC (minimum inhibiting concentration) and the widest spectrum of activity with respect to the number of strains they are able to kill.

Accordingly, MSH0704 and MSH0708 are the preferred peptides of the invention.

The peptides of the invention, as a further object of the invention, are also active against microbes. In particular, they have been tested and they resulted particularly active against *Staphylococcus aureus* and against *Pseudomonas aeruginosa*.

As a further object, the present invention relates to a pharmaceutical preparation comprising one or more of the peptides of the invention. In particular, said preparation may find use as an antimicrobial or, specifically, as a candidacidal medicament.

Moreover, the pharmaceutical preparation of the invention may include one or more other active principles, either candidacidal, thus possibly showing a synergistic effect, or not. In particular, there may be enclosed: antimicrobials, such as antibacterials, antifungals, antiviruses, antiparasitics, etc. or specifically other known candidacidal agents, such as, for instance, clotrimazole, nystatin, fluconazole, ketoconazole or, in case of more severe infections, amphotericin B, caspofungin, or voriconazole.

Dosages and dosage regimes may be established according to the kind of pathology and pharmaceutical form selected.

More in particular, the preparation of the invention may be formulated into a suitable administration pharmaceutical form for oral, including buccal or sublingual administration; rectal; nasal; topical, including buccal, sublingual or transdermal; vaginal; or parenteral, including subcutaneous, intramuscular, intravenous or intradermal route.

In particular, for oral administration, they can be prepared in the form of hard or soft capsules, tables, powders or granules; solutions syrups or suspensions in aqueous or non-aqueous liquids; edible foams or whips; or either oil-in-water or water-in-oil liquid emulsions; for topical administration, they can be prepared as ointments, creams, suspensions, lotions, powders, solutions, pastes, gels, sprays, aerosols or oils; for nasal administration sprays or drops may be prepared; for vaginal administration they may be prepared as pessaries, tampons, creams, gels, pastes, foams or spray formulations; for parenteral administration, aqueous and non-aqueous sterile injectable solutions or suspensions may be prepared.

The pharmaceutical forms above disclosed may comprise, in addition to the one or more peptides of the invention and according to the type of formulation, other additives or excipients conventional in the art, such as, for instance, diluent, solvents, bulking agents, fillers, reological modifier, stabilizers, binders, lubricants, disintegrant, preservatives, pH adjusting agents, buffers, antioxidant, chelating agents, plasticizer, polymers, emulsifiers, edulcorants, flavoring agents, etc, etc., alone or in combination thereof.

EXAMPLE 1

Inhibitory Activity Assays

Two *Candida albicans* isolates were purchased from the ATCC (No. 24433 and 76615). The other yeast isolates were obtained from the collection of Fondazione Ospedale Maggiore Policlinico, Mangiagalli e Regina Elena, Milano. The collection included *C. albicans* (7 isolates), *C. glabrata* (3 isolates), and *C. krusei* (3 isolates). Antifungal susceptibility testing was performed using the broth microdilution method according to the NCCLS M27-A guidelines (National Committee for Clinical Laboratory Standards. 1997, Reference method for broth dilution antifungal susceptibility testing of yeasts and approved standard NCCLS document M27-A. National Committee for Clinical Laboratory Standards, Wayne, Pa.). The organisms were removed from frozen glycerol stock (10% sterile glycerol suspensions stored at −70° C.), subcultured onto Sabouraud's dextrose plates, and incubated at 35° C. After 48 h of incubation, the plates were inspected for purity. To prepare stationary growth phase yeast, a colony was taken from the agar plate and transferred into 5 mL Sabouraud-dextrose broth and incubated for 48 h at 35° C. Cells were centrifuged at 1,000×g for 10 min and the pellet was washed twice with distilled water. Cells were counted and suspended in RPMI 1640 medium buffered to pH 7.0 with 0.165 mol $l^{-1}$ morpholinepropanesulphonic acid (MOPS) buffer (Sigma) to obtain the two times test inoculum ($1\times10^3$ to $5\times10^3$ CFU/mL). Each well of 96 U-shaped well-plates received 100 µl of each antifungal peptides in concentrations from $10^{-4}$ to $7.8\times10^{-7}$ M and 100 µl of the two-times inoculum to a final yeast concentration of $0.5\times10-2.5\times10$ cells $ml^{-1}$ The plates were incubated at 35° C. and were observed for growth at 48 h. The MIC90, i.e. the minimum inhibitory concentrations endpoint determined as 90% reduction in turbidity measured using a spectrophotometer (Titertek multiscan at 690 nm wave length).

EXAMPLE 2

Inhibitory Activity

The results of the assays performed according to Example 1 above are reported in Table 3 below, showing the MIC 90 at 48 hours, denoted as µg/ml concentration, for the peptide compounds of the invention.

TABLE 3

| Candida strain | Peptide | | | | | | |
| --- | --- | --- | --- | --- | --- | --- | --- |
| | MSH0701 | MSH0702 | MSH0703 | MSH0704 | MSH0705 | MSH0706 | MSH0707 |
| *C. albicans* | | | | | | | |
| ATCC 76615 | no | no | no | 61 | 117 | no | no |
| ATCC 24433 | no | no | no | 31 | 59 | no | no |
| 995439 | no | no | no | 31 | 59 | no | 118 |
| 995147 | no | no | no | 31 | 117 | no | no |
| 000954 | no | no | no | 61 | 117 | no | no |
| 991185 | no | no | no | 61 | 59 | no | no |
| 994199 | no | no | no | 31 | 59 | no | no |
| 983201-R1 | no | no | no | 61 | 117 | no | no |
| 011587 | no | 115 | no | 31 | 117 | no | no |
| *C. glabrata* | | | | | | | |
| 18012 | no | no | no | 122 | no | no | no |
| 995667 | no | no | no | 122 | no | — | no |
| 995651 | no | no | no | 122 | no | no | no |
| *C. krusei* | | | | | | | |
| 995668 | no | 115 | no | 61 | 117 | no | no |
| 991388 | no | 115 | no | 31 | 117 | no | 118 |
| 004490 | no | 115 | no | 31 | 117 | no | 118 |

TABLE 3-continued

| Candida strain | Peptide | | | | | |
|---|---|---|---|---|---|---|
| | MSH0708 | MSH0709 | MSH0710 | MSH0711 | MSH0712 | MSH0713 |
| *C. albicans* | | | | | | |
| ATCC 76615 | 31 | no | no | no | 60 | 122 |
| ATCC 24433 | 31 | no | no | no | 60 | 122 |
| 995439 | 31 | 117 | no | 118 | 60 | 122 |
| 995147 | 31 | no | no | no | 60 | 122 |
| 000954 | 31 | no | no | no | 60 | 122 |
| 991185 | 31 | 117 | no | no | 60 | 61 |
| 994199 | 31 | 117 | no | 118 | 60 | 61 |
| 983201-R1 | 61 | no | no | no | 60 | 122 |
| 011587 | 61 | 117 | no | 118 | 60 | 122 |
| *C. glabrata* | | | | | | |
| 18012 | 123 | no | no | no | no | no |
| 995667 | 123 | no | no | no | no | no |
| 995651 | 123 | no | no | no | no | no |
| *C. krusei* | | | | | | |
| 995668 | 61 | 117 | no | 118 | 119 | no |
| 991388 | 61 | 117 | no | 118 | 119 | 122 |
| 004490 | 31 | 117 | no | 118 | 60 | 122 |

The above data demonstrate that the most active compounds are MSH0704 and MSH0708.

EXAMPLE 3

Antibacterial Activity

In a further development of this invention we determined the antibacterial activity of peptides MSH 704 and 708.

The bacterial strains *Pseudomonas aeruginosa* ATCC 27853 and *Staphylococcus aureus* ATCC 29213 were grown in 2% Bacto Peptone water (Difco 1807-17-4) until growth was exponential. A standard microdilution technique with an inoculum of $2 \times 10^6$ CFU/mL was used. The minimal inhibitory concentration (MIC) of the peptides was determined in 1% Bacto Peptone water after incubation overnight at 37° C. The concentration range used for the peptides was $10^{-4}$ to $7.8 \times 10^{-7}$ M. MIC values of 31 µg/mL for *S. aureus* and 61 µg/mL for *P. aeruginosa* were found for both MSH 704 and 708.

```
-continued

H-His-D(2)-Nal-Arg-Trp-β-Ala-Lys-Phe-Val-NH₂

H-His-D(2)-Nal-Arg-Trp-Cha-Lys-Phe-Val-NH₂

H-His-D(2)-Nal-Arg-Trp-Cpa-Lys-Phe-Val-NH₂

H-His-D(2)-Nal-Arg-Trp-Acpc-Lys-Phe-Val-NH₂

H-His-D(2)-Nal-Arg-Trp-tBuGly-Lys-Phe-Val-NH₂

H-His-D(2)-Nal-Arg-Trp-Aic-Lys-Phe-Val-NH₂

H-His-D(2)-Nal-Arg-Trp-Cybu-Lys-Phe-Val-NH₂

H-His-D(2)-Nal-Arg-Trp-β-AA-Lys-Phe-Val-NH₂

H-His-D(2)-Nal-Arg-Trp-Aoca-Lys-Phe-Val-NH₂

H-His-D(2)-Nal-Arg-Trp-Phe-Lys-Phe-Val-NH₂.
```

The invention claimed is:

1. A peptide having a formula selected from a group of formulas consisting of:

H-His-D(2)-Nal-Arg-Trp-Gly-Gly-Lys-Phe-Val-NH₂

H-His-D(2)-Nal-Arg-Trp-Aib-Lys-Phe-Val-NH₂

2. A pharmaceutical preparation comprising one or more of the peptides of claim 1.

3. The pharmaceutical preparation of claim 2 further comprising one or more active principle selected from the group consisting of antibacterials, antifungals, antiviruses, and antiparasiticagents.

4. The pharmaceutical preparation of claim 3, wherein said antifungal agents are selected from the group consisting of clotrimazole, nystatin, fluconazole, ketoconazole, amphotericin B, caspofungin, and voriconazole.

5. The pharmaceutical preparation of claim 2, further comprising excipients and additives.

6. The pharmaceutical preparation of claim 2 for oral, rectal, nasal, topical, vaginal or parenteral administration.

7. The pharmaceutical preparation of claim 2, in the form of hard or soft capsules, tablets, granules, solutions syrups or suspensions in aqueous or non-aqueous liquids, edible foams or whips, oil-in-water or water-in-oil liquid emulsions, ointments, creams, suspensions, lotions, powders, solutions, pastes, gels, sprays, aerosols or oils, drops, pessaries, tampons, non-edible foams; aqueous or non-aqueous sterile injectable solutions or suspensions.

8. A method for the treatment of a patient affected by fungus or bacteria, comprising the step of administering to said patient an effective amount of a peptide according to claim 1.

9. The method of claim 8, wherein said microorganism is selected from *Candida* microorganisms.

10. The method of claim 9, wherein said *Candida* is selected from *Candida albicans, Candida glabrata* and *Candida krusei*.

11. The method of claim 8, wherein said peptide is active against *Candida* microorganisms.

12. The method of claim 8, wherein said microorganism is selected from *Staphylococcus aureus* and *Pseudomonas aeruginosa*.

\* \* \* \* \*

```
SEQUENCE LISTING

<160> NUMBER OF SEQ ID NOS: 1

<210> SEQ ID NO 1
<211> LENGTH: 4
<212> TYPE: PRT
<213> ORGANISM: Homo sapiens

<400> SEQUENCE: 1

His Phe Arg Trp
1
```